US010532016B2

(12) United States Patent
Hao et al.

(10) Patent No.: US 10,532,016 B2
(45) Date of Patent: Jan. 14, 2020

(54) ZINC-AMINO ACID-TRIPOLYPHOSPHATE COMPLEXES

(71) Applicant: Colgate-Palmolive Company, New York, NY (US)

(72) Inventors: Zhigang Hao, Bridgewater, NJ (US); Dennis Zhang, Piscataway, NJ (US); Donghui Wu, Bridgewater, NJ (US); Ravi Subramanyam, Belle Mead, NJ (US); Chi-Yuan Cheng, Hillsborough, NJ (US); Long Pan, Somerset, NJ (US); Stanislav Jaracz, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/213,871

(22) Filed: Dec. 7, 2018

(65) Prior Publication Data

US 2019/0175479 A1 Jun. 13, 2019

Related U.S. Application Data

(60) Provisional application No. 62/598,208, filed on Dec. 13, 2017.

(51) Int. Cl.
*A61K 8/58* (2006.01)
*A61Q 11/00* (2006.01)
*A61Q 17/00* (2006.01)
*A61Q 15/00* (2006.01)

(52) U.S. Cl.
CPC ............... *A61K 8/58* (2013.01); *A61Q 11/00* (2013.01); *A61Q 15/00* (2013.01); *A61Q 17/005* (2013.01); *A61K 2800/58* (2013.01)

(58) Field of Classification Search
None
See application file for complete search history.

(56) References Cited

U.S. PATENT DOCUMENTS

| 3,538,230 | A | | 11/1970 | Pader et al. |
| 3,862,307 | A | | 1/1975 | Digiulio |
| 3,937,807 | A | | 2/1976 | Haefele |
| 3,959,458 | A | | 5/1976 | Agricola |
| 4,051,234 | A | | 9/1977 | Gieske et al. |
| 4,340,583 | A | | 7/1982 | Wason |
| 5,004,597 | A | | 4/1991 | Majeti et al. |
| 5,032,389 | A | * | 7/1991 | Chan ............ A61Q 11/00 424/57 |
| 5,188,821 | A | | 2/1993 | Gaffar et al. |
| 5,192,531 | A | | 3/1993 | Gaffar et al. |
| 5,763,657 | A | * | 6/1998 | Hijiya ........... C07C 229/26 426/807 |
| 9,763,865 | B2 | * | 9/2017 | Pan ............ A61K 8/27 |
| 10,130,571 | B2 | | 11/2018 | Szewczyk |
| 10,195,125 | B2 | * | 2/2019 | Pan ............ A61K 8/27 |
| 2019/0091117 | A1 | | 3/2019 | Szewczyk |

FOREIGN PATENT DOCUMENTS

| EP | 0428493 | 5/1991 |
| WO | 2015/195124 | 12/2015 |

OTHER PUBLICATIONS

International Search Report and Written Opinion of the International Searching Authority in International Application No. PCT/US2018/064576, dated Mar. 8, 2019.

Mitchell et al., 1979, "On the position of the intramolecular equilibrium between opened and aromatic-ring stacked forms in ternary complexes composed of adenosine 5'-triphosphate, Mg2+ or Zn2+, and L-tryptophanate, and in related ternary systems," Helvetica Chimica Acta 62(6):1723-1735.

* cited by examiner

*Primary Examiner* — Brian J Davis (57) ABSTRACT

Disclosed herein are zinc-amino acid-tripolyphosphate complexes, oral care and personal care compositions comprising zinc-amino acid-tripolyphosphate complexes, and methods of making and using the same.

20 Claims, 8 Drawing Sheets

ZINC-AMINO ACID-TRIPOLYPHOSPHATE COMPLEXES

CROSS-REFERENCE TO RELATED APPLICATIONS

This application claims priority to and the benefit of U.S. Provisional Application No. 62/598,208, filed on Dec. 13, 2017, the contents of which are hereby incorporated by reference in its entirety.

BACKGROUND

Dental erosion involves demineralization and damage to the tooth structure due to acid attack from nonbacterial sources. Erosion is found initially in the enamel and, if unchecked, may proceed to the underlying dentin. Dental erosion is generally caused by acids attack on the dentin enamel. The source of such acids is primarily from the growth of cariogenic bacteria, which secrete such organic acids as acetic acid and lactic acid, and erosion may be further caused or exacerbated by acidic foods and drinks. The tooth enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally, saliva has a slightly basic pH between 7.2 to 7.4, although in the vicinity of plaque caused by cariogenic bacteria, the local pH may be considerably lower. When the pH is lowered, and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form divalent cations, $Zn^{2+}$. Zinc has been shown to have antibacterial properties in plaque and caries studies.

Both insoluble and soluble zinc salts have been used in dentifrice and mouthwash compositions, but there can be associated several disadvantages. First, fully solubilized free zinc ions in solution can impart an unpleasant, astringent mouthfeel, which makes formulating an oral care composition to provide effective levels of zinc, and also have acceptable organoleptic properties, can be difficult. In addition, in some formulations, free zinc ions will react with anionic surfactants such as sodium lauryl sulfate, thus interfering with foaming and cleaning. Zinc oxide and insoluble zinc salts, on the other hand, may do a poor job of delivering zinc to the teeth because of their insolubility. The antibacterial effectiveness of various soluble and insoluble zinc salts can also be affected by interactions with other components.

Zinc salts have been used for antibacterial activity in both oral care and personal care products. In oral care products, zinc salts promote oral health by inhibiting the growth of cariogenic bacteria. In personal care products, such as antiperspirants and deodorants, zinc salts promote efficacy by inhibiting the growth of the bacteria which causes odor. Complexes of zinc with basic amino acids and halide anions have been shown to be effective in both oral care and personal care compositions.

While the prior art discloses the use of various oral compositions for the treatment of dentinal hypersensitivity, dental caries, and enamel erosion and demineralization, and personal care compositions for antiperspirant and deodorant activity, there is still a need for additional compositions and methods which provide improved performance for such uses.

BRIEF SUMMARY

It has now been discovered that zinc ions can form a soluble complex with an amino acid and tripolyphosphate anion. The complex comprising zinc and an amino acid, e.g., a basic amino acid, with tripolyphosphate anion forms an anionic complex which may, optionally, combine with one or more cations to form a neutral or cationic complex or salt. When placed in an oral care or personal care formulation, this complex provides an effective concentration of zinc ions for antibacterial activity, for example, delivering an antibacterial effective amount of zinc to the tooth enamel, thereby protecting against erosion and reducing bacterial colonization and biofilm development, and/or delivering an antibacterial effective amount of zinc to the skin, thereby reducing bacterial colonization and body odor. While providing efficient delivery of zinc in comparison to oral care formulations with insoluble zinc salts, the oral care formulations comprising the zinc-amino acid-tripolyphosphate complex do not exhibit the poor taste and mouthfeel, poor fluoride delivery, and poor foaming and cleaning associated with conventional zinc-based oral care products using soluble zinc salts.

In some embodiments, the amino acid of the complex is a basic amino acid, for example, lysine or arginine. In one particular embodiment, the zinc-amino acid-tripolyphosphate complex is a zinc-lysine-tripolyphosphate complex, for example, the novel complex designated ZLP, which may be formed from a mixture of zinc oxide, lysine, and sodium tripolyphosphate. ZLP has the chemical structure $[Zn(C_6H_{14}N_2O_2)(P_3O_{10})Na_4]^+$, and may exist in solution as the cationic cation $([Zn(C_6H_{14}N_2O_2)(P_3O_{10})Na_4]^+)$ and a chloride anion, or may be a solid salt, e.g., $[Zn(C_6H_{14}N_2O_2)(P_3O_{10})Na_4]^+Cl^-$. In some embodiments, the ZLP complex may exist as the sodium-free trivalent anion, $[Zn(C_6H_{14}N_2O_2)(P_3O_{10})]^{3-}$. As a result, in the presence of added monovalent or divalent cations, such as lithium, potassium, calcium, and magnesium, other complex ions can result, for example $[Zn(C_6H_{14}N_2O_2)(P_3O_{10})Ca_2]^+$, $[Zn(C_6H_{14}N_2O_2)(P_3O_{10})K_4]^+$, $[Zn(C_6H_{14}N_2O_2)(P_3O_{10})Li_4]^+$, $[Zn(C_6H_{14}N_2O_2)(P_3O_{10})Mg_2]^+$), and the like, including complex ions comprising mixed alkali and alkaline earth metal species, such as $[Zn(C_6H_{14}N_2O_2)(P_3O_{10})Na_2Ca]^+$.

The invention thus provides zinc-amino acid-polyphosphate complexes, such as zinc-lysine-tripolyphosphate (ZLP) and zinc-arginine-tripolyphosphate, per se, as well as oral care products that deliver zinc to the oral cavity and personal care products that deliver zinc to the skin, as well as methods of making and using zinc-amino acid-polyphosphate complexes, such as ZLP.

The invention thus provides oral care compositions, for example mouthwash, oral gel or dentifrice compositions, that comprise a zinc-amino acid-tripolyphosphate complex, e.g., a zinc-lysine-tripolyphosphate complex or zinc-arginine-tripolyphosphate complex, e.g., the ZLP complex. The compositions may optionally further comprise a fluoride source and or an additional phosphate source. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

The invention further provides antiperspirant or deodorant compositions that comprise zinc-amino acid-tripolyphosphate complexes, such as zinc-lysine-tripolyphosphate or zinc-arginine-tripolyphosphate, e.g., ZLP. The invention also encompasses other personal care compositions for application to the skin, for example hand soaps or body washes, comprising zinc-amino acid-polyphosphate complexes, such as zinc-lysine-tripolyphosphate or zinc-arginine-tripolyphosphate, e.g., ZLP.

The invention further provides oral care methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

The invention further provides methods of using the compositions of the invention to reduce sweat and/or body odor, comprising applying a composition of the invention to the skin, hair or body.

The invention further provides methods of making the compositions of the invention comprising combining a zinc ion source (e.g., zinc oxide), an amino acid (e.g., a basic amino acid, e.g., arginine or lysine, in free or salt form or hydrate form), and a tripolyphosphate source, for example combining zinc oxide and lysine hydrochloride in aqueous solution, e.g. at a molar ratio of Zn:amino acid of 1:1 to 1:3, e.g., 1:1 and at a molar ratio of Zn:tripolyphosphate of 1:1 to 1:3, e.g., 1:1; optionally isolating the ionic complex thus formed as a solid; and admixing with an oral care or personal care base.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention therefore provides, in a first embodiment, a zinc-amino acid-tripolyphosphate complex (Complex 1). "Zinc-amino acid-tripolyphosphate complex" refers to a complex which comprises at least one zinc center, at least one amino acid residue, and at least one tripolyphosphate moiety, wherein the amino acid residue and the tripolyphosphate moiety are each coordinated, ionically, covalently or by Lewis electron pair donation (coordination), to the zinc center. For example, 1.1 Complex 1, wherein the amino acid (AA) is a basic amino acid (BAA).
1.2 Complex 1.1, wherein the amino acid is arginine or lysine.
1.3 Complex 1, et seq., wherein the complex comprises a zinc center, an amino acid residue and a tripolyphosphate moiety.
1.4 Complex 1, et seq., wherein the complex further comprises one or more alkali metal or alkaline earth metal ions, for example, lithium, sodium, potassium, calcium or magnesium, or combinations thereof
1.5 Any preceding complex, wherein the zinc center, the amino acid residue and the tripolyphosphate moiety are arranged such that the amino acid and the tripolyphosphate are each coordinated to the zinc center, e.g., by an ionic bonding, covalent bonding or coordinate covalent bonding.
1.6 Any preceding complex, wherein the zinc center is divalent zinc.

Figure 1A:
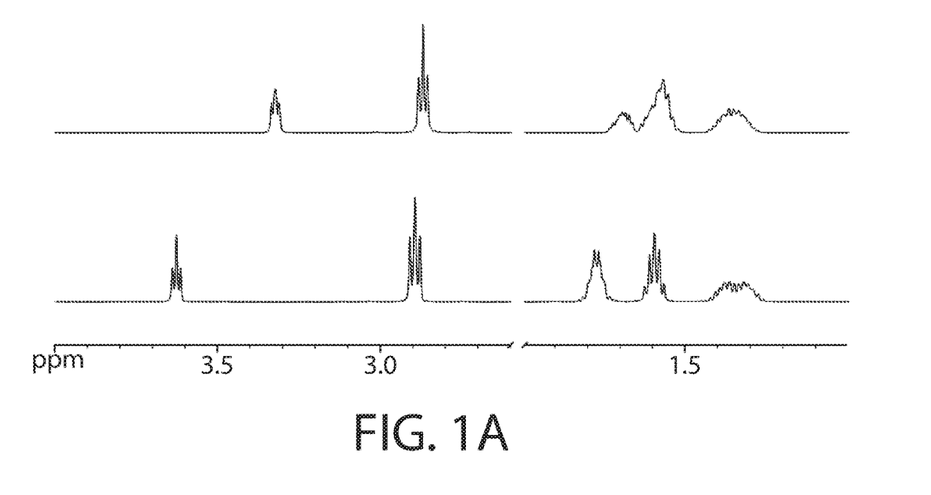
FIG. 1(a) shows the proton-NMR spectrum of the ZLP complex.
Figure 1B:
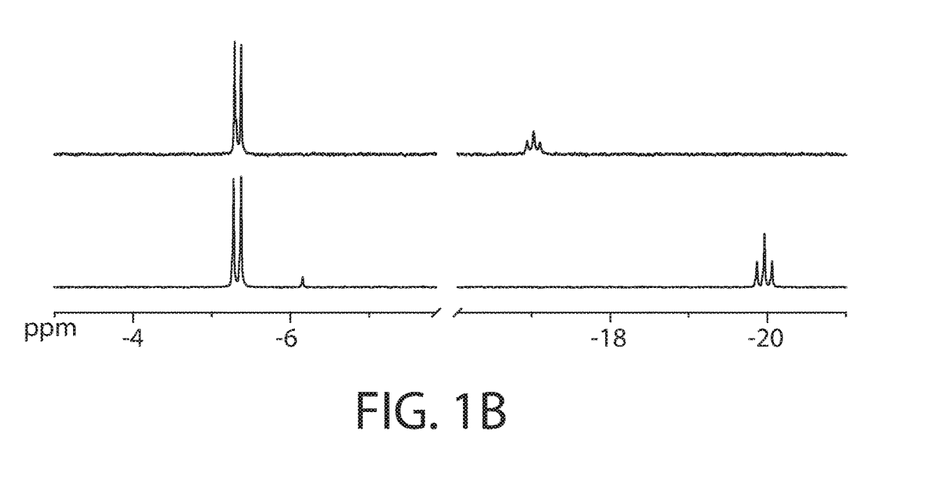
FIG. 1(b) shows the phosphorus-NMR spectrum of the ZLP complex.
Figure 1C:
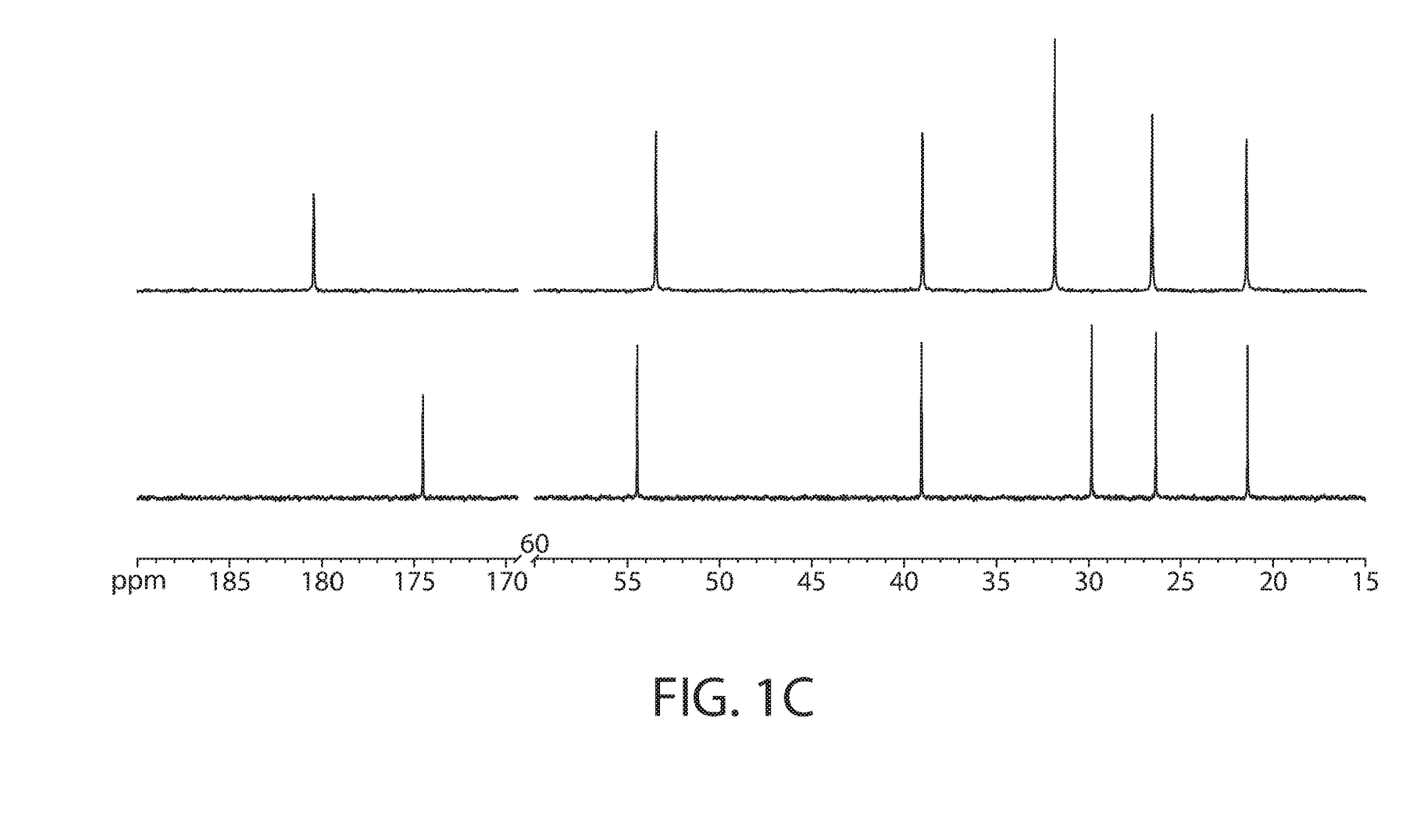
FIG. 1(c) shows the carbon-NMR spectrum of the ZLP complex.

1.7 Any preceding complex, wherein the complex comprises zinc and amino acid in a 1:1 to 1:3 molar ratio, e.g., a 1:1 molar ratio,
1.8 Any preceding complex, wherein the complex comprises zinc and tripolyphosphate in a 1:1 to 1:3 molar ratio, e.g., a 1:1 molar ratio.
1.9 Any preceding complex, wherein the complex comprises tripolyphosphate and amino acid in a 1:1 to 1:3 molar ratio, e.g., a 1:1 molar ratio.
1.10 Any preceding complex, wherein the complex further comprises one or more monovalent cations selected from lithium, sodium and potassium, in a molar ratio of zinc to cation of 1:1 to 1:5, e.g., 1:1, 1:2, 1:3, 1:4 or 1:5.
1.11 Any preceding complex, wherein the complex further comprises one or more divalent cations selected from calcium and magnesium, in a molar ratio of zinc to cation of 1:1 or 1:2.
1.12 Any preceding complex, wherein the complex consists of a zinc center, an amino acid, a tripolyphosphate anion and optionally one or more divalent or monovalent cations, such that the entire coordination complex has a net charge selected from −3, −2, −1, 0, or +1.
1.13 Any preceding complex, wherein the complex has the structure $[Zn(AA)(P_3O_{10})Na_4]^+$, optionally wherein the complex exists in solution as a cation $([Zn(AA)(P_3O_{10})Na_4]^+)$ and a monovalent anion, e.g., a chloride anion, wherein AA is an amino acid, e.g., lysine or arginine.
1.14 Any preceding complex, wherein the complex is a salt, e.g. a solid salt, having the structure $[Zn(AA)(P_3O_{10})Na_4]^+X^-$, wherein X is a monovalent anion, such as chloride, bromide, iodide or hydroxide, wherein AA is an amino acid, e.g., lysine or arginine.
1.15 Any preceding complex, wherein the complex exists as a trivalent anion, $[Zn(AA)(P_3O_{10})]^{3-}$, optionally in the presence of additional monovalent or divalent cations, such as lithium, potassium, calcium, and magnesium, optionally forming other complex ions with these cations, such as $[Zn(AA)(P_3O_{10})Ca_2]^+$, $[Zn(AA)(P_3O_{10})K_4]^+$, $[Zn(AA)(P_3O_{10})Li_4]^+$, $[Zn(AA)(P_3O_{10})Mg_2]^+)$, and the like; wherein AA is an amino acid, e.g., lysine or arginine.
1.16 Any preceding complex, wherein the complex has a three-dimensional structure wherein the zinc center is coordinated to the alpha-amino group of the amino acid (e.g., via the alpha-amino nitrogen), and the carboxylic acid group of the amino acid (e.g., via the carboxylate oxygen), and wherein the zinc center is also coordinated to three of the tripolyphosphate group oxygen atoms (e.g., the anionic oxygen atoms), optionally wherein the tripolyphosphate group is further coordinated via its anionic oxygen atoms to one to four monovalent cations (e.g. sodium) or two divalent cations (e.g. calcium).
1.17 Any preceding complex, wherein the complex is the ZLP complex, as defined herein.
1.18 Complex 1.17, wherein the complex shows as its major mass spectral peaks ions of m/z 554.3, 556.3 and 558.3 (each +/−0.6).
1.19 Complex 1.17 or 1.18, wherein the complex has the proton NMR spectrum shown in FIG. 1(a) and/or the phosphorus NMR spectrum shown in FIG. 1(b) and/or the carbon NMR spectrum shown in FIG. 1(c).
1.20 Any preceding complex, wherein the complex is formed by combining zinc oxide, an amino acid (optionally amino acid hydrohalide) and an alkali metal or alkaline earth metal tripolyphosphate (e.g., sodium tripolyphosphate).
1.21 Any preceding complex, wherein the complex is formed by combining zinc oxide, an amino acid hydrohalide (e.g., amino acid hydrochloride) and sodium tripolyphosphate.
1.22 Any preceding complex, wherein the complex is formed by combining zinc oxide, lysine hydrochloride and sodium tripolyphosphate,
1.23 Any preceding complex, wherein the molar ratio of zinc oxide to amino acid to tripolyphosphate is from 1-3:1-3:1-3, e.g., 1:1:1.
1.24 Any preceding complex, wherein the complex forms in-situ in an oral care composition or personal care composition upon admixture of the zinc oxide, amino acid and tripolyphosphate.

The invention therefore provides, in a second embodiment, an oral care or personal care composition (Composition 1), comprising Complex 1 or any of Complexes 1.1-1.24; e.g., 1.1. Composition 1, wherein the complex is present in an amount to provide the zinc in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight.
1.2. Composition 1 or 1.1, wherein the complex is present in an amount to provide the amino acid in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.
1.3. Composition 1, 1.1 or 1.2, wherein the complex is present in an amount to provide the tripolyphosphate in an amount of 0.05 to 20% by weight of the composition, optionally at least 0.1, at least 0.2, at least 0.3, at least 0.4, at least 0.5, at least 1, at least 2, at least 3, at least 4, at least 5, at least 10, or at least 15, up to 20% by weight, e.g., about 1-10% by weight.
1.4. Any of the foregoing compositions wherein the composition is an oral care composition, e.g., selected from a dentifrice, toothpaste, tooth powder, gel, or mouthwash.
1.5. Any of the foregoing compositions, wherein the composition is a personal care composition, e.g., selected from an antiperspirant, deodorant, skin cleaner (e.g. soap or body wash), or hair cleaner (e.g. shampoo).
1.6. Any foregoing composition, wherein the composition does not provide any precipitate when the composition is diluted with water, e.g., when the composition is diluted with water during use by the consumer.
1.7. Any of the foregoing compositions further comprising an effective amount of a fluoride ion source, e.g., providing 500 to 3000 ppm fluoride.
1.8. Any of the foregoing compositions further comprising an effective amount of fluoride, e.g., wherein the fluoride source is selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.9. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.10. Any of the foregoing compositions comprising buffering agents, e.g., sodium phosphate buffer (e.g., sodium phosphate monobasic and disodium phosphate).

1.11. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

1.12. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.13. Any of the preceding compositions further comprising a viscosity modifying amount of one or more of polysaccharide gums, for example xanthan gum or carrageenan, silica thickener, and combinations thereof.

1.14. Any of the preceding compositions further comprising flavoring, fragrance and/or coloring.

1.15. Any of the foregoing compositions further comprising a cosmetically acceptable carrier comprising one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

1.16. Any of the foregoing compositions further comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.17. Any of the preceding compositions further comprising a whitening agent, e.g., a selected from the group consisting of peroxides, metal chlorites, perborates, percarbonates, peroxyacids, hypochlorites, and combinations thereof.

1.18. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.19. Any of the preceding compositions further comprising a breath freshener, fragrance or flavoring.

1.20. Any of the foregoing compositions, wherein the pH of the composition is approximately neutral, e.g., from pH 6 to pH 9 e.g., 7 to 9, or 7 to 8, or 7 to 7.5 or 7.5 to 8, or about pH 7.5.

1.21. Any of the foregoing compositions, wherein the composition comprises water in an amount of less than 10% by weight, e.g., from 0.1 to 10%, or 0.1 to 5% or 0.1 to 3%, by weight of the composition.

1.22. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

1.23. Any of the foregoing compositions for use to reduce body odor and or reduce perspiration.

The invention further provides a method to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a complex of the invention, e.g., any of Complex 1, et seq., or a composition of the invention, e.g., any of Composition 1, et seq. to the teeth or oral cavity of a person in need thereof.

The invention further provides a method of reducing perspiration, reducing body odor, or killing bacteria on the skin or hair, comprising applying the complex of the invention, e.g., any of Complex 1, et seq., or a composition of the invention, e.g., any of Composition 1, et seq. to the skin, hair or body.

The invention further provides a method of making a complex of the invention, e.g., any of Complex 1, et seq., the method comprising the steps of combining zinc oxide, amino acid, and alkali metal or alkaline earth metal tripolyphosphate in a suitable solvent, adjusting the pH, and isolating the resulting product, optionally as a solid salt. The pH is preferably adjusted to between 8 and 10. The temperature of the reaction is preferably maintained at between 30° C. and 70° C., e.g., about 50° C.

The invention further provides a method of making a composition of the invention, e.g., any of Composition 1, et seq., comprising adding a purified complex of the invention, e.g., any of Complex 1, et seq., to a suitable oral care or personal care base composition, and further adding any additional oral care or personal care excipients or ingredients to produce an oral care composition or personal care composition. In some embodiments, the oral care or personal care base composition is a dentifrice or mouthwash base, or an antiperspirant or deodorant base.

In various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Complexes 1, et seq., or any of Compositions 1, et seq. as described above, to the oral cavity of a person in need thereof, e.g., one or more times per day. The invention further provides Complexes 1, et seq. and Compositions 1, et seq. for use in any of these methods.

It will be understood that although the zinc, amino acid, and tripolyphosphate, may be present in a composition (e.g., an oral care or personal care composition) primarily in the form of precursor materials (e.g., zinc oxide, amino acid or amino acid hydrohalide, and alkali metal or alkaline earth metal tripolyphosphate) or in the form of the Complex of the invention, e.g., any of Complex 1 et seq., there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

Oral care compositions of the invention include any oral care formulation known in the art, for example a toothpaste, gel, mouthwash, powder, cream, strip, gum, or any other known in the art.

The benefits of the oral care compositions of the invention are numerous. By providing zinc ions and zinc containing compounds that can release zinc ions in oral cavities, the oral care compositions of the invention provide antimicrobial, antiplaque, anti-gingivitis, anti-malodor, anti-caries, and anticalculus benefits. Additional benefits include but are not limited to anti-attachment, anti-periodontitis and anti-bone loss, as well as promotion of wound healing.

A second benefit is the anti-erosive properties of zinc ions, which form anti-erosive deposits on tooth surfaces through oxidation and hydrolysis. The surface deposits of zinc species can react with and neutralize acids, thus protecting the dental surface from the erosive effects of the acids. In this regard, the more surface deposition the treatments lead to, the more efficacious the treatments are. It is also noted that when the surface deposits neutralize acids, beneficial zinc ions and amino acids can be released, providing oral care benefits other than anti-erosion.

A third benefit is the benefit associated with amino acids. The surface deposits contain the corresponding amino acids, such as arginine and lysine. These amino acids can provide multiple benefits. For example, basic amino acids lead to higher pH of the plaque and can provide anti-caries benefits. In addition, it is also expected that arginine can enhance the activity of arginolytic bacteria, leading to a more-healthy plaque.

Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments, the amino acid is a neutral or acidic amino acid, e.g., glycine. In some embodiments, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminopropanoic acid, salts thereof or combinations thereof. In certain embodiments, the amino acid is lysine. In other embodiments, the amino acid is arginine.

In certain embodiments, the Compositions described herein, i.e., Compositions 1, et seq., comprise the zinc-amino acid-tripolyphosphate complex in an amount of 0.05 to 10% by weight of the composition. In certain embodiments, precursors, e.g., zinc oxide, amino acid or amino acid hydrohalide, and alkali or alkaline earth metal tripolyphosphate, are present in amounts such that when combined into the composition to form the zinc-amino acid-tripolyphosphate complex in situ, said complex would be present in an amount of 0.05 to 10% by weight of the composition. In either of these embodiments, the amount of the complex can be varied for the desired purpose, such as a dentifrice or a mouthwash. In other embodiments, the amount of the complex is at least 0.1, at least 0.2, at least 0.3, at least 0.4, at least 0.5, at least 1, at least 2, at least 3, or at least 4 up to 10% by weight of the composition. In other embodiments, the amount of the complex is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, Composition 1, et seq., comprises zinc in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the composition is anhydrous. By anhydrous, it is meant that there is less than 5% by weight water, optionally less than 4, less than 3, less than 2, less than 1, less than 0.5, or less than 0.1% water, down to 0%, by weight water.

When provided in an anhydrous composition, precursors, e.g., zinc oxide, amino acid or amino acid hydrohalide, and alkali metal or alkaline earth metal tripolyphosphate, may not significantly react to form the complex of the invention. When contacted with a sufficient amount of water, which can be in the form of saliva and/or water used to rinse the mouth during or after application of the composition, or which be in the form of water used during cleansing or bathing the skin or hair or water from perspiration, the precursors will react to form the complex of the invention.

The carrier represents all other materials in the composition other than the zinc-amino acid-tripolyphosphate complex or its precursors. The amount of carrier is then the amount to reach 100% by adding to the weight of the zinc amino acid halide, including any precursors.

Oral Care Active Agents: The compositions of the invention may comprise various agents which are active to protect and enhance the strength and integrity of the enamel and tooth structure and/or to reduce bacteria and associated tooth decay and/or gum disease, including or in addition to the zinc—amino acid—halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouth rinse. For example, a triclosan toothpaste may contain about 0.3 wt % triclosan.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives: The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming agents: The oral care compositions of the invention also may include an agent to increase the amount of foam that is produced when the oral cavity is brushed. Illustrative examples of agents that increase the amount of foam include, but are not limited to, polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions useful in the invention may contain anionic surfactants, for example:
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).
  iv. higher alkyl aryl sulfonates such as sodium dodecyl benzene sulfonate (sodium lauryl benzene sulfonate)
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar control agents: In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents: The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers: The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water: The oral compositions may comprise significant levels of water. Water employed in the preparation of commercial oral compositions should be deionized and free of organic impurities. The amount of water in the compositions includes the free water which is added plus that amount which is introduced with other materials.

Humectants: Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other optional ingredients: In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional anti-plaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Synthesis of ZLP Complex

The general reaction for formation of ZLP is as follows:

$$ZnO + Lysine \cdot HCl + Na_5P_3O_{10} \rightarrow [Zn(Lysine)(Na_4P_3O_{10})]^+Cl^-(ZLP)$$

About 6.0 g of lysine hydrochloride is dissolved in 250 ml distilled water with stirring at room temperature. About 12.0 g sodium tripolyphosphate pentabasic is added with stirring, followed by either 50% aqueous sodium hydroxide solution or concentrated hydrochloric acid solution to adjust the pH to either 5, 6, 7, 8, 9 or 10. To the resulting solution, about 2.68 g of zinc oxide is slowly added. The mixture is then allowed to stir at either room temperature, 50° C. or 80° C., for 2 hours. The reaction is monitored by liquid chromatography-mass spectrometry (LC-MS, using electrospray ionization-tandem mass spectrometer running positive ion mode). LC separation is achieved on Agilent Zorbax SB-Aq column (2.1 mm i.d.×50 mm, 3.5 μm particle size), running 5% water/methanol at 70 μL/minute with 1 μL injection volume.

Apparent yield of the ZLP complex is found to be about maximal at pH 8-10, with about 50% lower yields at pH 5 and 6. Apparent yield of the ZLP complex is found to be maximal at a temperature of 50° C., while it is about 40% lower at 80° C., and about 60% lower at room temperature.

Laboratory scale-up synthesis of ZLP: 96 g of lysine hydrochloride is dissolved in 4000 ml distilled water with stirring at room temperature. 193.3 g sodium tripolyphosphate pentabasic is added with stirring, followed by 50% aqueous sodium hydroxide to adjust the pH to about 9. To the resulting solution, 42.79 g of zinc oxide is slowly added. The mixture is then allowed to stir at room temperature for 2 hours. Upon completion of the reaction, the reaction is filtered to afford a pure aqueous solution of ZLP complex. The ZLP is analyzed by LC-MS and NMR.

Characterization of ZLP: Mass Spectrometry: LC-MS is conducted on purified ZLP, under the LC-MS conditions described above. The ZLP complex is shown consist of a single complex with typical zinc triplets in a cluster at m/z 554.5, 556.8 and 558.5. Each of these three isotopic parent peaks is shown to fragment into a primary daughter ion of m/z 408.5/410.5/412.6, consistent with loss of lysine to yield a tetrasodium zinc-tripolyphosphate complex.

Characterization of ZLP: Nuclear Magnetic Resonance Spectroscopy. NMR studies are performed on a Bruker Avance spectrometer with a 5 mm BBO probe operating at 500.0 MHz for proton NMR, 125.7 MHz for carbon-13 NMR, and 202.4 MHz for phosphorus-31 NMR. Proton shifts are reported relative to the water signal at 4.8 ppm. Phosphorus shifts are referred to 85% phosphoric acid as the externals standard.

ZLP's proton NMR spectrum is shown in FIG. 1(a), the phosphorus NMR spectrum is shown in FIG. 1(b), and the carbon-NMR spectrum is shown in FIG. 1(c). The proton spectrum of ZLP compared to lysine free base shows a significant shift in the alpha-proton from 3.6 ppm in lysine to 3.3 ppm in ZLP. Additionally, one of the two geminal beta-protons is shifted and split into two peaks near 1.65 ppm. This suggests that the amino and carboxylic acid groups are both bonded to the zinc center in ZLP, resulting in chemically nonequivalent beta protons. In the carbon spectra, the carbonyl carbon of lysine is shifted from 175 ppm to 180 ppm in ZLP, consistent with metallic bonding of the carboxyl group to zinc. The alpha and beta carbons also show shifting. The phosphorus NMR spectrum show that the central phosphorus of the tripolyphosphate chain is significantly shifted from −20 ppm in STPP to −17 ppm in ZLP, consistent with the central phosphate group coordinating to the zinc center. Taken together, these NMR and MS data support the following structure for the ZLP complex:

Chemical Formula: $C_6H_{14}N_2Na_4O_{12}P_3Zn^+$

Example 2

Toothpaste Composition Comprising ZLP Complex

A toothpaste composition comprising 7.25 wt % purified ZLP is prepared according to the formula shown in Table 1. The composition comprises 0.85% by weight zinc.

TABLE 1

| Ingredients | Wt % |
|---|---|
| Sodium carboxymethyl cellulose | 0.65 |
| Polyethylene glycol | 3% |
| Sorbitol, 70% Aq. Soln. | 50% |
| Distilled water | Q.S. |
| Sodium Fluoride | 0.24 |
| High Cleaning Silica | 10 |
| Abrasive Silica | 10 |
| Thickening Silica | 2.75 |
| Sodium Lauryl Sulfate | 1.5 |
| Cocamidopropylbetaine | 1.25 |
| Flavors/Colors/Sweeteners | 1.50 |
| ZLP Complex | 7.25 |
| Total | 100 |

Example 3

Stability of ZLP Complex

Dilution experiment: A solution of ZLP in distilled water at a concentration of 200 mg/mL (23.6 wt % zinc) is prepared. For comparison, a solution of zinc-lysine-chloride complex (ZLC) ([Zn(lysine)$_2$Cl]Cl) is prepared at a concentration of 185 mg/mL. Both solutions are diluted with water at ratios from 1:2 to 1:16. It is found that for the ZLP solution, no precipitation occurs at any dilution, demonstrating the stability of the ZLP complex in solution. In contrast, at dilutions of 1:8 to 1:16 the ZLC complex shows significant precipitation of insoluble material. In addition, the undiluted ZLP solution is stored at room temperature for one month, followed by repeat LC-MS analysis, and it is found that the LC-MS spectrum has not changed from that obtained initially.

Foaming experiment: A solution of ZLP in distilled water at a concentration of 7.25 wt % (0.85 wt % zinc) containing also 2 wt % of sodium lauryl sulfate is compared to a solution of ZLC and sodium lauryl sulfate at the same concentrations and to a solution of sodium lauryl sulfate. Each solution is sealed in a screw-cap vial and shaken back and forth ten times. It is observed that the amount of foaming in the aqueous SLS solution is comparable to the foaming in the ZLP/SLS solution, but that foaming is significantly inhibited in the ZLC/SLS solution. This shows that while ZLC complex interacts negatively with anionic surfactants such as SLS, ZLP does not. A similar experiment is conducted using an 1:10 aqueous slurry of the toothpaste formula of Example 1 compared to a control toothpaste having the same composition except for the absence of ZLP (in the control, the 7.25% ZLP is replaced by 0.5 wt % TSPP and 6.75 wt % sorbitol, 70%). After shaking these suspensions, it is observed that there is comparable foaming between the two.

Polyphosphate experiment: Aqueous solutions of ZLP and ZLC, respectively, are prepared as described above, and 5 mL of each of these solutions is mixed with 5 mL STPP solution at a concentration of 2 wt %. It is observed that the combination of ZLP and STPP solution remains clear and homogenous, while the mixture of ZLC solution and STPP solution produces a white precipitate. Thus, ZLP complex is stable in the presence of additional STPP, whereas other zinc complexes may not be.

Example 4

Demonstration of ZAP Complex by Titration

Titration Experiments: The formation of zinc-arginine-tripolyphosphate complexes in aqueous solution is demonstrated by performing titration experiments. Titration is a method known in the art for identifying stable aqueous complex species. See, for example, Mitra R P, Dharmarha O P, *The Reaction Between Polyvalent Metal Cations and Alkali Metal Pyrophosphates*. PROC NATL INST SCI INDIA. 26: 151 (1960); Teki K, Bhat R, *Estimation of the Components in Oral Care products Available in Indian Market—Part II: Toothpaste*. INT J PHARM CHEM SCI. 2(2):705-712 (2013).

In the single component titration procedure, a scintillation vial (20 mL) is loaded with 2 mL of a 0.25M zinc nitrate solution and 6 mL of distilled water. The vial is stirred on a magnetic stir plate with an immersed pH electrode. Initial pH is measured. While stirring, the solution is slowly titrated with a 0.75M aqueous solution of arginine in small portions (e.g., 0.01-0.1 mL). In between each addition, the solution is allowed to equilibrate and the pH is recorded. At the conclusion of the experiment, the molar equivalent of added arginine is plotted against the pH. The slope is calculated and plotted as well to highlight the inflection points, which indicate where complex formation takes places.

Substantially the same single-component titration procedure is also performed in a titration of 0.75M zinc chloride with 0.25M sodium tripolyphosphate.

A dual-component titration procedure is also performed. A 1:1 solution of zinc to tripolyphosphate (0.625M each) is first prepared by mixing 2 mL of the 0.25M zinc nitrate solution with 2 mL of 0.25M sodium tripolyphosphate solution and 4 mL of distilled water. The titration procedure is performed as described for the single-component method.

Substantially the same dual-component titration procedure is also performed in a titration of a 1:1 zinc nitrate/arginine solution (0.625M each) with 0.25M sodium tripolyphosphate.

The results of the titration experiments are shown in FIGS. 2-5. The inflection points present in the first derivative plots are indicative of the formation of stable complexes between the species present in solution.

Figure 2:
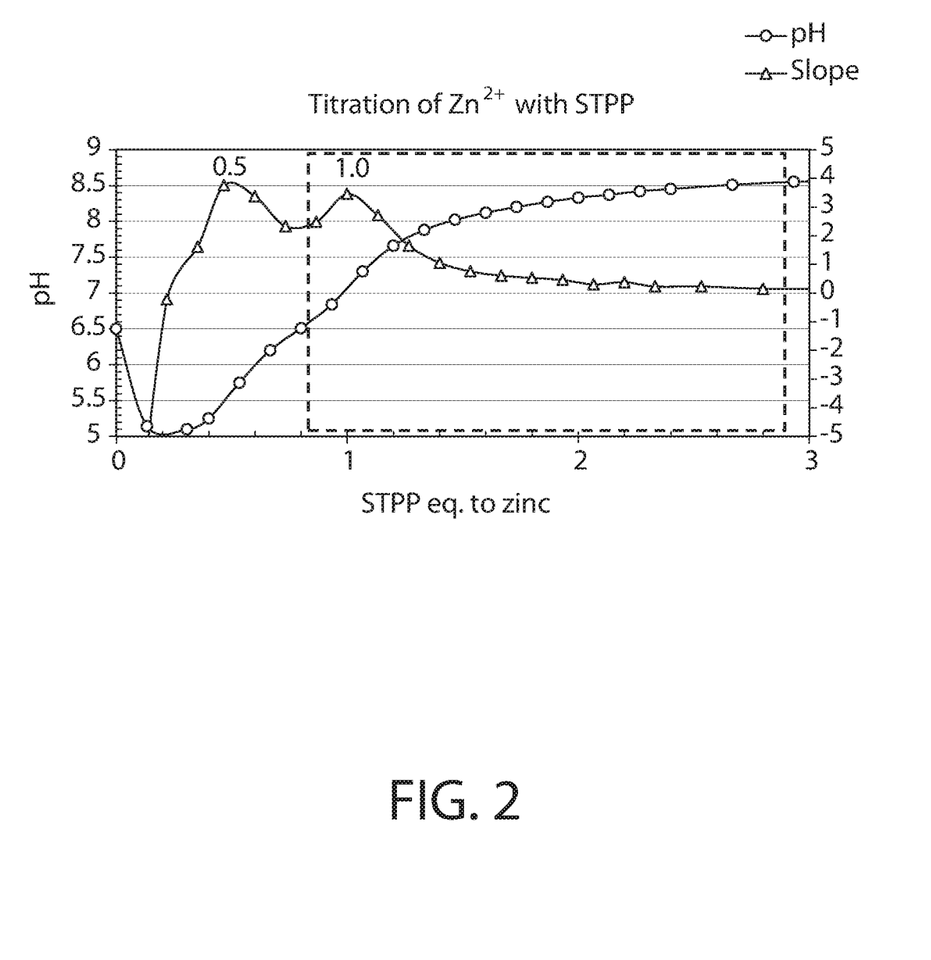
FIG. 2 shows a titration plot for titration of zinc chloride solution with sodium tripolyphosphate solution. The curve marked with spheres represents pH, while the curve marked with triangles represents slope. The area enclosed by dashes represents the conditions under which the solution was clear.

The results show that zinc chloride and sodium tripolyphosphate (STPP) react in both 2:1 and 1:1 ratios, to form, respectively, $NaZn_2(P_3O_{10})$ and $Na_3Zn(P_3O_{10})$ complexes (see FIG. 2). From the beginning of the titration until approximately 1 equivalent of STPP was added, the reaction solution was cloudy, indicating that while the 2:1 complex is poorly soluble, the 1:1 complex is soluble.

Figure 3:
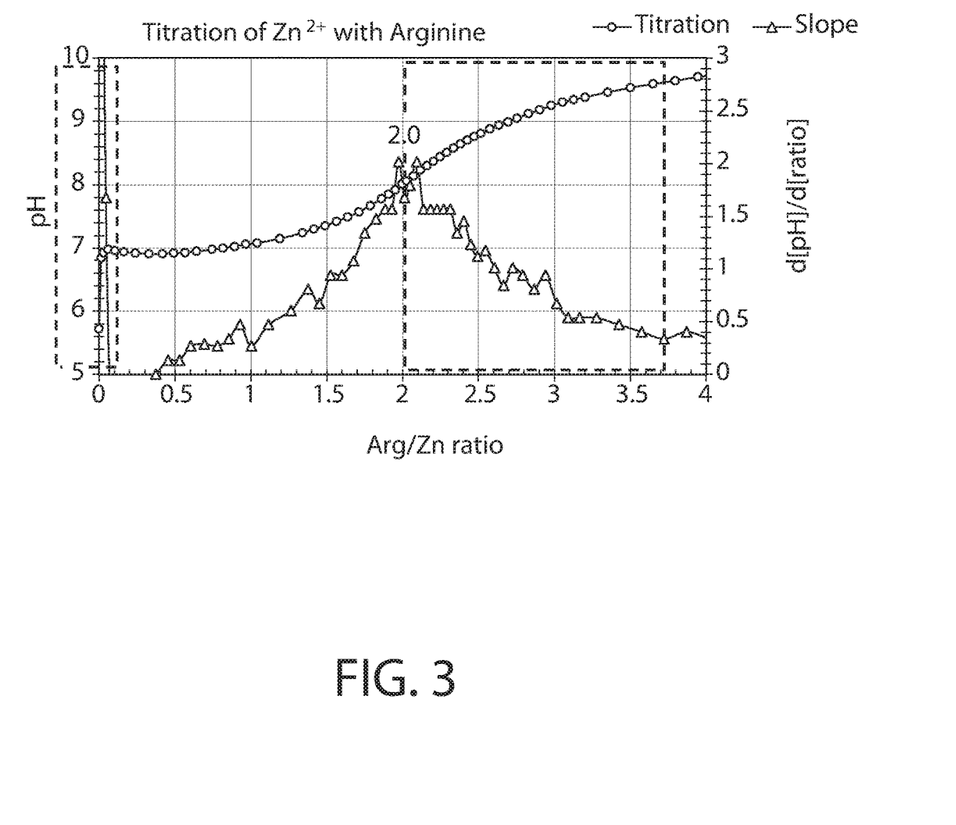
FIG. 3 shows a titration plot for titration of zinc nitrate solution with arginine solution. The curve marked with spheres represents pH, while the curve marked with triangles represents slope. The area enclosed by dashes represents the conditions under which the solution was clear.
Figure 4:
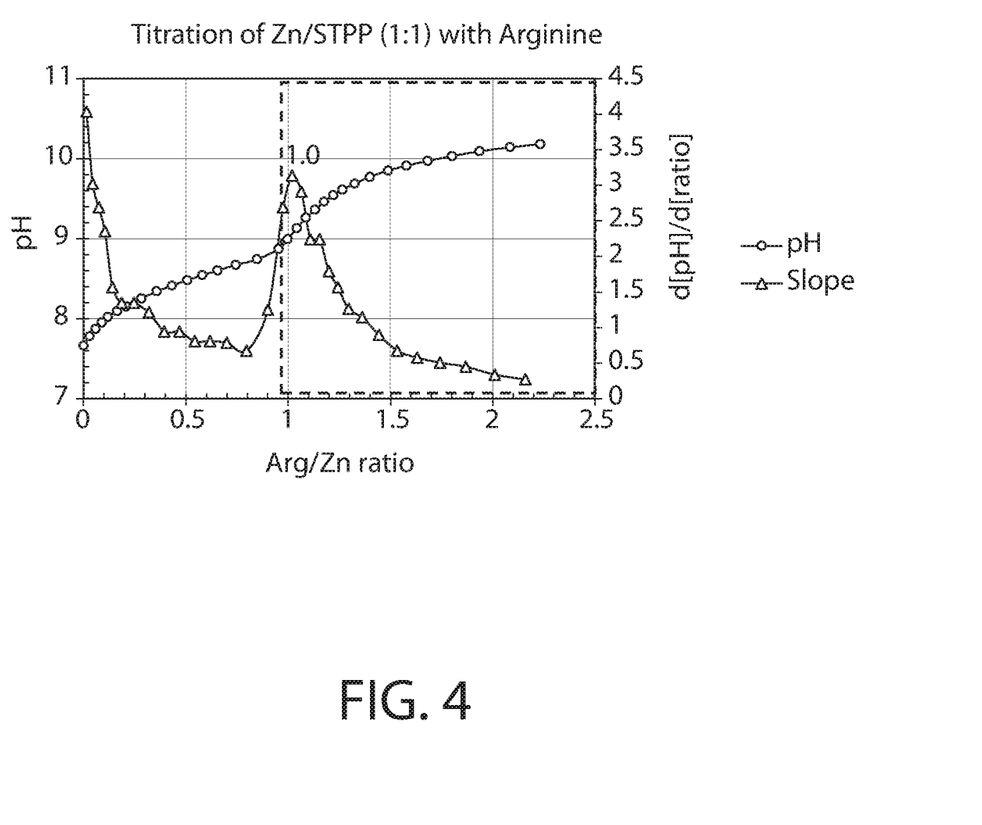
FIG. 4 shows a titration plot for titration of a 1:1 zinc nitrate/sodium tripolyphosphate solution with arginine solution. The curve marked with spheres represents pH, while the curve marked with triangles represents slope. The area enclosed by dashes represents the conditions under which the solution was clear.
Figure 5:
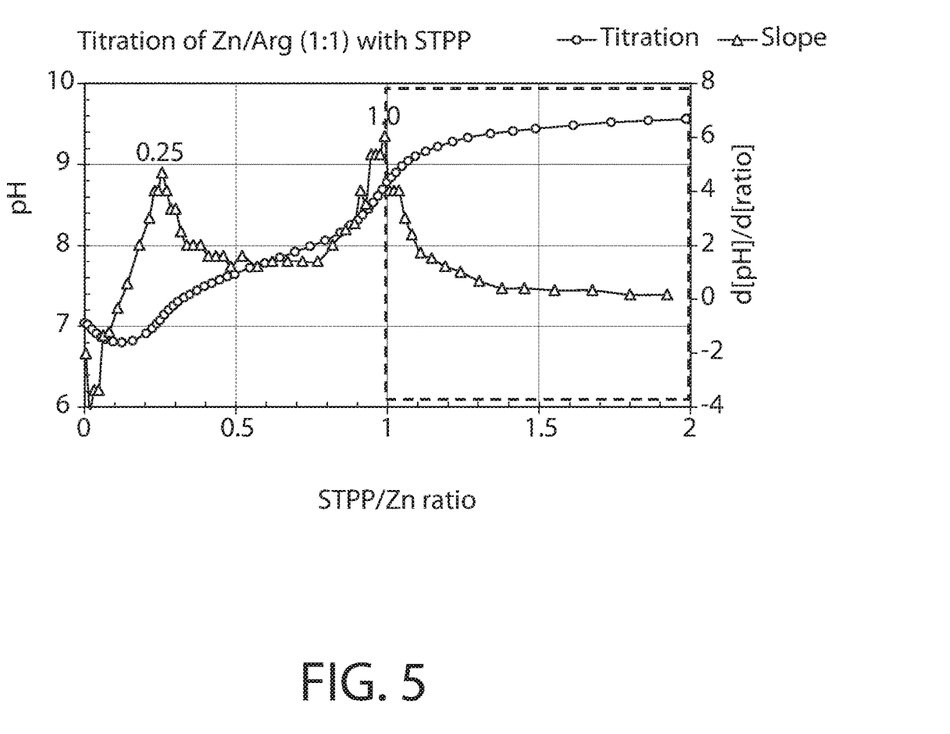
FIG. 5 shows a titration plot for titration of a 1:1 zinc nitrate/arginine solution with sodium tripolyphosphate solution. The curve marked with spheres represents pH, while the curve marked with triangles represents slope. The area enclosed by dashes represents the conditions under which the solution was clear.

The results further show that zinc nitrate and arginine react in a 1:2 ratio to form a $Zn(arginine)_2$ complex (see FIG. 3). The results further show that the zinc nitrate/STPP solution reacts with arginine at a 1:1:1 ratio, suggesting the formation of a mixed complex, such as $Na_3Zn(Arg)(P_3O_{10})$ (see FIG. 4). The results further show that the zinc nitrate/arginine solution reacts with STPP solution at both 4:4:1 and 1:1:1 ratios (see FIG. 5). The former result suggests that initially individual zinc-arginine, $Zn(arginine)_2$, and zinc-STPP, $NaZn_2(P_3O_{10})$, complexes are forming, consistent with the results shown in FIG. 1. The 1:1:1 ratio suggests formation of a zinc-arginine-tripolyphosphate complex of the formula $Na_3Zn(Arg)(P_3O_{10})$, consistent with the results shown in FIG. 4. This is also consistent with the data shown above for the formation of 1:1:1 zinc-lysine-tripolyphosphate complexes.

Example 5

Demonstration of ZLP Complex by Titration

Substantially the same procedures as shown above in Example 4 are performed to demonstrate the formation of ZLP complex by titration, thus validating the procedure employed in Example 4.

Figure 6:
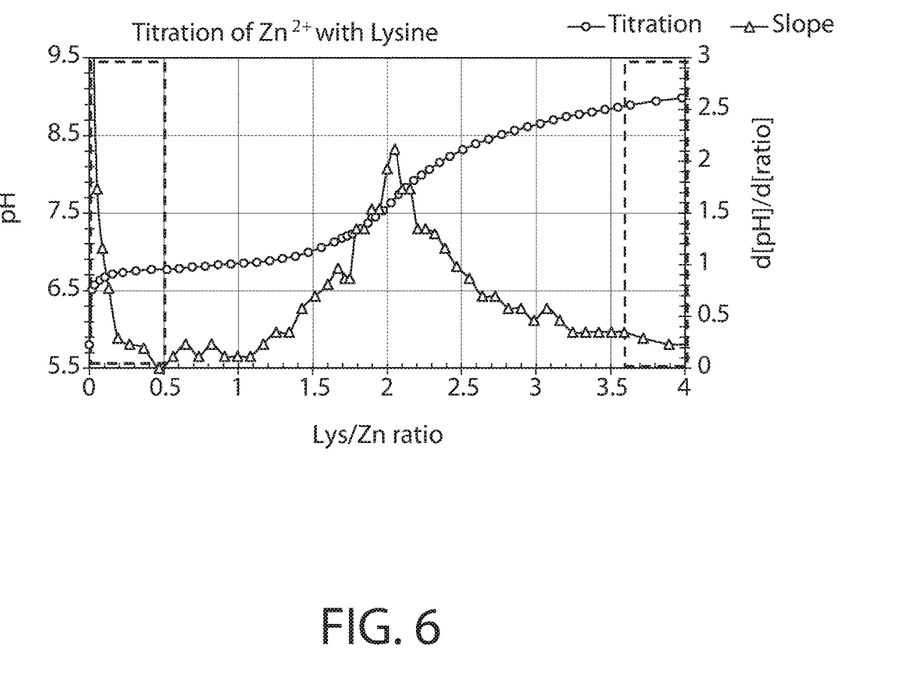
FIG. 6 shows a titration plot for titration of zinc nitrate solution with lysine solution. The curve marked with spheres represents pH, while the curve marked with triangles represents slope. The area enclosed by dashes represents the conditions under which the solution was clear.
Figure 7:
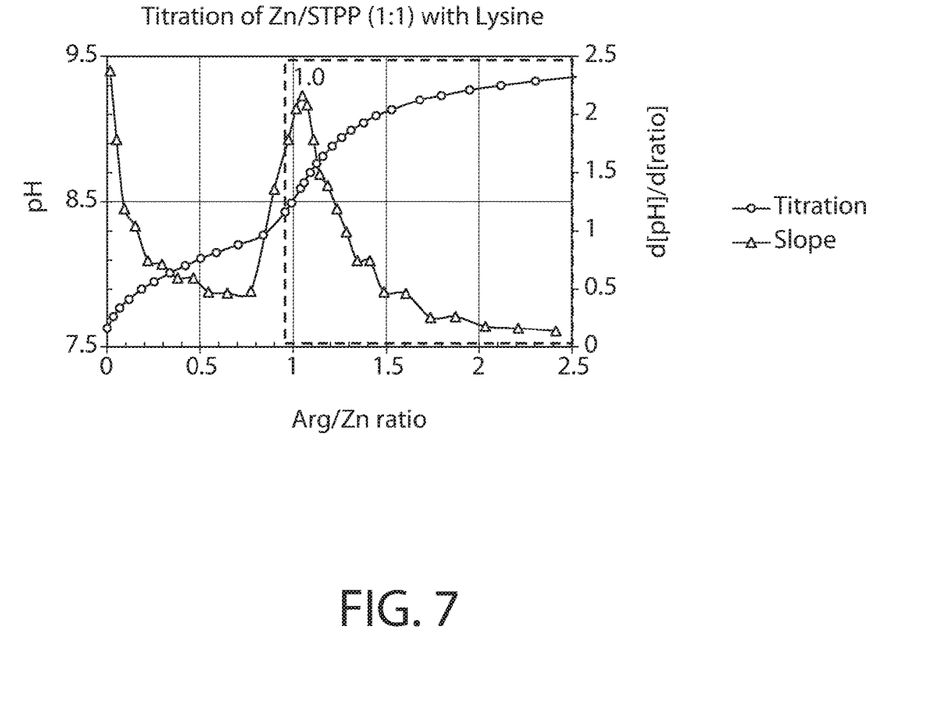
FIG. 7 shows a titration plot for titration of a 1:1 zinc nitrate/sodium tripolyphosphate solution with lysine solution. The curve marked with spheres represents pH, while the curve marked with triangles represents slope. The area enclosed by dashes represents the conditions under which the solution was clear.

A single component titration between 0.25M zinc nitrate solution and 0.75M lysine solution is conducted as described above for and arginine. The result is shown in FIG. 6. A dual component titration between a 1:1 solution of zinc nitrate/sodium tripolyphosphate (0.625M each) and 0.75M lysine solution is also conducted, as described above for arginine. The result is shown in FIG. 7. These results are consistent with the results obtained using arginine, and they demonstrate that zinc nitrate and lysine react in a 1:2 ratio to form a $Zn(lysine)_2$ complex (FIG. 6) and that zinc nitrate/STPP solution reacts with lysine at a 1:1:1 ratio to form a $Na_3Zn(Lys)(P_3O_{10})$ complex (FIG. 7).

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed:

1. A complex consisting of zinc, amino acid, and tripolyphosphate, and optionally one or more alkali metals.

2. The complex of claim 1, wherein the amino acid is a basic amino acid.

3. The complex of claim 1 wherein the complex consists of a zinc center, an amino acid residue, a tripolyphosphate moiety and one to four alkali metal cations.

4. The complex of claim 1, wherein the complex further comprises one or more alkali metal ions.

5. The complex of claim 3, wherein the zinc center, the amino acid residue and the tripolyphosphate moiety are arranged such that the amino acid and the tripolyphosphate are each coordinated to the zinc center.

6. The complex of claim 1, wherein the complex consists of a zinc center, an amino acid, a tripolyphosphate anion and optionally one or more alkali metal cations, such that the entire coordination complex has a net charge selected from −3, −2, −1, 0, or +1.

7. The complex of claim 1, wherein the complex has the structure $[Zn(AA)(P_3O_{10})Na_4]^+$, and wherein AA is a basic amino acid.

8. The complex of claim 1, wherein the complex is formed by combining zinc oxide, an amino acid (or amino acid hydrohalide), and an alkali metal tripolyphosphate.

9. An oral care or personal care composition comprising a zinc-amino acid-tripolyphosphate complex.

10. The composition of claim 9, wherein the complex is present in an amount to provide the zinc in an amount of 0.05 to 10% by weight of the composition.

11. The composition of claim 9, wherein the complex is present in an amount to provide the amino acid in an amount of 0.05 to 30% by weight of the composition.

12. The composition of claim 9, wherein the complex is present in an amount to provide the tripolyphosphate in an amount of 0.05 to 20% by weight of the composition.

13. The composition of claim 9, wherein the composition is an oral care composition.

14. The composition of claim 9, wherein the composition is a personal care composition.

15. A method to reduce and inhibit acid erosion of the enamel, clean the teeth, reduce bacterially-generated biofilm and plaque, reduce gingivitis, inhibit tooth decay and formation of cavities, and/or reduce dentinal hypersensitivity, comprising applying an effective amount of the complex according to claim 1 to the teeth or oral cavity of a person in need thereof.

16. A method of reducing perspiration, reducing body odor, or killing bacteria on the skin or hair, comprising applying an effective amount of the complex according to claim 1 to the skin, hair or body.

17. The complex of claim 2, wherein the amino acid is arginine or lysine.

18. The complex of claim 4, wherein the one or more alkali metal ions are selected from lithium, sodium, potassium, or combinations thereof.

19. The complex of claim 7, wherein AA is arginine or lysine.

20. The complex of claim 7, wherein the complex exists in solution as a cation ($[Zn(AA)(P_3O_{10})Na_4]+$) and a monovalent anion.

* * * * *

UNITED STATES PATENT AND TRADEMARK OFFICE
CERTIFICATE OF CORRECTION

PATENT NO. : 10,532,016 B2
APPLICATION NO. : 16/213871
DATED : January 14, 2020
INVENTOR(S) : Zhigang Hao et al.

Page 1 of 1

It is certified that error appears in the above-identified patent and that said Letters Patent is hereby corrected as shown below:

In the Specification

In Column 4, Line 59, after "thereof", insert -- . --.

In the Claims

In Column 22, Line 27, in Claim 20, replace "($[Zn(AA)(P_3O_{10})Na_4]+$)" with -- ($[Zn(AA)(P_3O_{10})Na_4]^+$) --.

Signed and Sealed this
Fourteenth Day of April, 2020

Andrei Iancu
*Director of the United States Patent and Trademark Office*